(12) United States Patent
Gustafson et al.

(10) Patent No.: US 11,612,448 B2
(45) Date of Patent: Mar. 28, 2023

(54) MEDICAL EQUIPMENT ADAPTABLE TRAVEL RESTRAINT SYSTEMS

(71) Applicant: Children's Medical Center Corporation, Boston, MA (US)

(72) Inventors: Kathryn Jean Gustafson, Waltham, MA (US); Michele Linda DeGrazia, Lakeville, MA (US)

(73) Assignee: Children's Medical Center Corporation, Boston, MA (US)

( * ) Notice: Subject to any disclaimer, the term of this patent is extended or adjusted under 35 U.S.C. 154(b) by 247 days.

(21) Appl. No.: 16/818,223

(22) Filed: Mar. 13, 2020

(65) Prior Publication Data
US 2020/0289231 A1 Sep. 17, 2020

Related U.S. Application Data

(60) Provisional application No. 62/817,868, filed on Mar. 13, 2019.

(51) Int. Cl.
| | | |
|---|---|---|
| *B65D 30/00* | (2006.01) | |
| *A61B 50/13* | (2016.01) | |
| *A61B 50/31* | (2016.01) | |
| *A45C 5/14* | (2006.01) | |
| *A45C 5/03* | (2006.01) | |
| *A61B 50/30* | (2016.01) | |

(52) U.S. Cl.
CPC ............... *A61B 50/13* (2016.02); *A45C 5/14* (2013.01); *A61B 50/31* (2016.02); *A45C 2005/032* (2013.01); *A61B 2050/3011* (2016.02); *A61B 2560/0437* (2013.01)

(58) Field of Classification Search
CPC . A61B 2050/3011; A61B 50/13; A61B 50/31; A61B 2560/0437; A45C 5/14; A45C 2005/032
USPC .......... 206/570–572; 224/418, 427; 190/102, 190/110–113; 280/47.29, 47.24
See application file for complete search history.

(56) References Cited

U.S. PATENT DOCUMENTS

| | | | | |
|---|---|---|---|---|
| 4,513,866 A | * | 4/1985 | Thomas ................... | A61F 17/00 190/110 |
| 5,207,303 A | * | 5/1993 | Oswalt ................. | A61B 50/312 206/570 |
| 9,027,721 B1 | * | 5/2015 | Osborne .................. | A45C 5/06 190/110 |
| 2005/0183913 A1 | * | 8/2005 | Godshaw ............... | A45C 13/04 190/18 R |
| 2006/0011686 A1 | * | 1/2006 | Latham ..................... | B60R 7/04 190/102 |
| 2009/0255770 A1 | * | 10/2009 | Slater ....................... | A45C 9/00 190/107 |

OTHER PUBLICATIONS

Pro Rack, "Gas Control Products", https://www.prorackgasproducts.com/2020, 4 Pages.

* cited by examiner

*Primary Examiner* — Luan K Bui
(74) *Attorney, Agent, or Firm* — Strategic Patents, P.C.

(57) ABSTRACT

A medical equipment adaptable travel restraint system includes a number of features to support transportation and use of durable medical equipment including crash-safe transportation in a vehicle, vehicle-to-site transportation by a user for deployment, and operation of the durable medical equipment by the user without removal from a carrier of the medical equipment adaptable travel restraint system.

18 Claims, 6 Drawing Sheets

MEDICAL EQUIPMENT ADAPTABLE TRAVEL RESTRAINT SYSTEMS

RELATED APPLICATIONS

This application claims priority to U.S. Prov. App. No. 62/817,868, filed on Mar. 13, 2019, the entire content of which is hereby incorporated by reference.

BACKGROUND OF THE INVENTION

According to a national survey, approximately 10.2 million children under the age of 18 have special health care needs. Children with Special Health Care Needs ("CSHCN") are children with an increased risk of a chronic physical, developmental, behavioral, or emotional condition, and who require health services beyond that required by children generally. Such children often require various forms of assistive technology and/or durable medical equipment to provide for their healthcare needs. Durable medical equipment includes items such as cardiorespiratory and oxygen saturation monitors, feeding pumps, suction apparatuses, oxygen tanks, and other related medical supplies. Although often described in the context of pediatric patients, embodiments may also have potential for use in other patient populations that use durable medical equipment, such as adults and elderly with chronic illness (e.g., those requiring enteral feedings, suctioning, and supplemental oxygen). All such patients or other care receivers that might benefit from the use of a transportation system for durable medical equipment, or other individuals transporting or using the durable medical equipment to provide care for such patients, are referred to generally herein as users.

Recent downsizing of durable medical equipment allows CSHCN and other users to travel more freely with their medical equipment. However, the storage of portable durable medical equipment during motor vehicle travel remains problematic. Current recommendations for storing durable medical equipment in motor vehicles do not appear to ensure that the equipment will not become dislodged and become a dangerous projectile or explosive resulting in significant bodily injury to the motor vehicle occupants during a crash. An observational study examining transportation practices of CSHCN and their families revealed that only a small number of drivers properly restrain durable medical equipment in their vehicles.

There remains a need for an improved transportation system for durable medical equipment, e.g., that mitigates potential crash hazards while facilitating transportation and use.

SUMMARY

A medical equipment adaptable travel restraint system includes a number of features to support transportation and use of durable medical equipment including crash-safe transportation in a vehicle, vehicle-to-site transportation by a user for deployment, and operation of the durable medical equipment by the user without removal from a carrier of the medical equipment adaptable travel restraint system.

In one aspect, a system for medical equipment transportation described herein includes a carrier including a rigid shell and an internal equipment restraint system for securely restraining a medical feed pump system within an interior of the carrier; a containment chamber on an exterior of the carrier, the containment chamber adapted to store one or more accessories for the medical feed pump system, and the containment chamber including a window for viewing contents of the containment chamber; a progressive restraint system for distributing a load of the carrier along a length of a three-point vehicle seatbelt of a passenger seat in a passenger vehicle when the carrier is placed in the passenger seat and the three-point vehicle seatbelt is deployed through the progressive restraint system and around the carrier; an access port in the carrier adapted to provide physical access by a user to a control for the medical feed pump system while the medical feed pump system is in the carrier without requiring removal of the medical feed pump system from the carrier; and a transportation system including a number of wheels and a telescoping handle to facilitate wheeled transportation of the carrier between the passenger vehicle and a deployment site.

The medical feed pump system may include a feed pump weighing at least five pounds, and the internal equipment restraint system and the progressive restraint system may cooperate to retain the medical feed pump system in the carrier and the passenger seat against at least 20 g forces in a forward direction relative to the passenger vehicle and at least 0.5 g forces in a reverse direction and a lateral direction relative to the passenger vehicle.

The system may include shoulder straps for securing the carrier to shoulders of a wearer for transportation.

In another aspect, a system for durable medical equipment transportation described herein includes a carrier including an internal equipment restraint system for securely restraining durable medical equipment within the carrier; one or more containment chambers adapted to store one or more accessories for the durable medical equipment; a vehicle restraint system for coupling the carrier to a passenger vehicle; an access port in the carrier adapted to provide access by a user to the durable medical equipment during use; and a transportation system to facilitate transportation of the carrier between the passenger vehicle and a deployment site.

The internal equipment restraint system and the vehicle restraint system may cooperate to restrain the durable medical equipment against at least 1 g forces in a forward direction relative to the passenger vehicle and at least 0.5 g forces in a reverse direction and a lateral direction relative to the passenger vehicle. The durable medical equipment may have a weight of at least one pound or at least five pounds. The carrier may include a rigid shell or a non-rigid nylon shell.

The vehicle restraint system may include one or more straps for securing the system to a back of a car seat. The vehicle restraint system may include a progressive restraint system for distributing a load of the carrier along a length of a three-point vehicle seatbelt when the carrier is placed in a passenger seat of the passenger vehicle and the three-point vehicle seatbelt is deployed through the progressive restraint system and around the carrier. The vehicle restraint system includes one or more connectors adapted to engage corresponding ISOFIX anchors in the passenger vehicle.

The system may include a base configured to be coupled to one or more ISOFIX anchors in the passenger vehicle, and wherein the vehicle restraint system includes one or more connectors for removably and replaceably coupling the carrier to the base.

The internal equipment restraint system may be shaped and sized to secure an oxygen tank. The internal equipment restraint system may be shaped and sized to secure a feeding pump. The internal equipment restraint system may be shaped and sized to secure one or more of an intravenous pump, an oxygen monitor, a pulse oximeter, and a suction apparatus.

The one or more containment chambers may be shaped and sized to hold one or more of medical tubing, sanitary wipes, needles, gauze, and feed pump bags. The access port may include an opening for physical access to the durable medical equipment. The opening may provide physical access to a control panel for the durable medical equipment.

The transportation system may include wheels on a bottom surface of the carrier. The transportation system may also or instead include a telescoping handle for transporting the carrier. The transportation system may include shoulder straps for securing the carrier on shoulders of a wearer.

The access port may be a viewport providing visual access to the durable medical equipment. The viewport may include one or more of a mesh window or a clear plastic window. The viewport may provide a view of a control panel for the durable medical equipment. The one or more containment chambers may include a window formed of a mesh material or a clear plastic for viewing contents of the one of the containment chambers. The system may include a reinforcement for securely retaining the contents of the one of the containment chambers. The reinforcement includes at least one of a webbing or a buckle to securely restrain the contents.

The system may include a telescoping pole that extends from the carrier, the telescoping pole including an arm to hold an intravenous fluid bag or a feeding bag.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views.

DETAILED DESCRIPTION

In the following document, references to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated, and each separate value within such a range is incorporated into the specification as if it were individually recited herein. Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (as well as fractions thereof unless the context clearly dictates otherwise).

The words "about," "approximately" or the like, when accompanying a numerical value or physical property, are to be construed as indicating a deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose or the like. Ranges of values and/or numeric values are provided herein as examples only, and do not constitute a limitation on the scope of the described embodiments unless explicitly stated otherwise. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," and the like, are words of convenience and are not to be construed as limiting terms.

As used herein, the term "motor vehicle" includes automobiles, cars, buses, airplanes, boats, trains, and the like. Embodiments of the present teachings can, for example, restrain cardiorespiratory monitors, oxygen saturation monitors, feeding pumps, suction apparatuses, oxygen tanks, and other medical equipment during travel in a motor vehicle. Additionally, terms such as "seat," "car seat," "passenger seat," "vehicle seat," and "motor vehicle seat" are used interchangeably to refer to a seat for a passenger in any such motor vehicle unless a more specific meaning is otherwise explicitly provided or clear from the context.

As used herein, durable medical equipment refers to any medical equipment that might usefully be transported and restrained during transportation, as described herein. For example, embodiments of durable medical equipment may include cardiorespiratory monitors, oxygen saturation monitors, feeding pumps, suction apparatuses, oxygen tanks, pulse oximeters, and other medical supplies, along with accessories such as feeding bags, hoses, batteries, sterile wipes, gauze, and so forth.

A number of "connectors" are described herein for various purposes such as securing a medical equipment adaptable travel restraint system (MEATR system) to a vehicle, for securing components of the MEATR system to one another, or for securing an item of durable medical equipment, or an accessory for the item of durable medical equipment, to the MEATR system. It will be understood that, while specific examples of connectors are provided throughout this description, any such connector suitable for a particular context may be used as a connector for the purposes described herein. Thus, for example, a connector may include a buckle, a strap, a Velcro strip, a zipper, a sleeve, an anchor, a cinch, a button, a snap, a tie, a zip tie, a string, a cleat, a flap, a harness, mesh webbing, a bungie, a grommet, a clip, and so forth, as well as any other connector(s) for connecting, disconnecting, and reconnecting one item to another, and any combination of the foregoing, and all such connectors and combinations may be used as the connectors described herein, unless a different meaning is explicitly provided or otherwise clear from the context.

Figure 1:
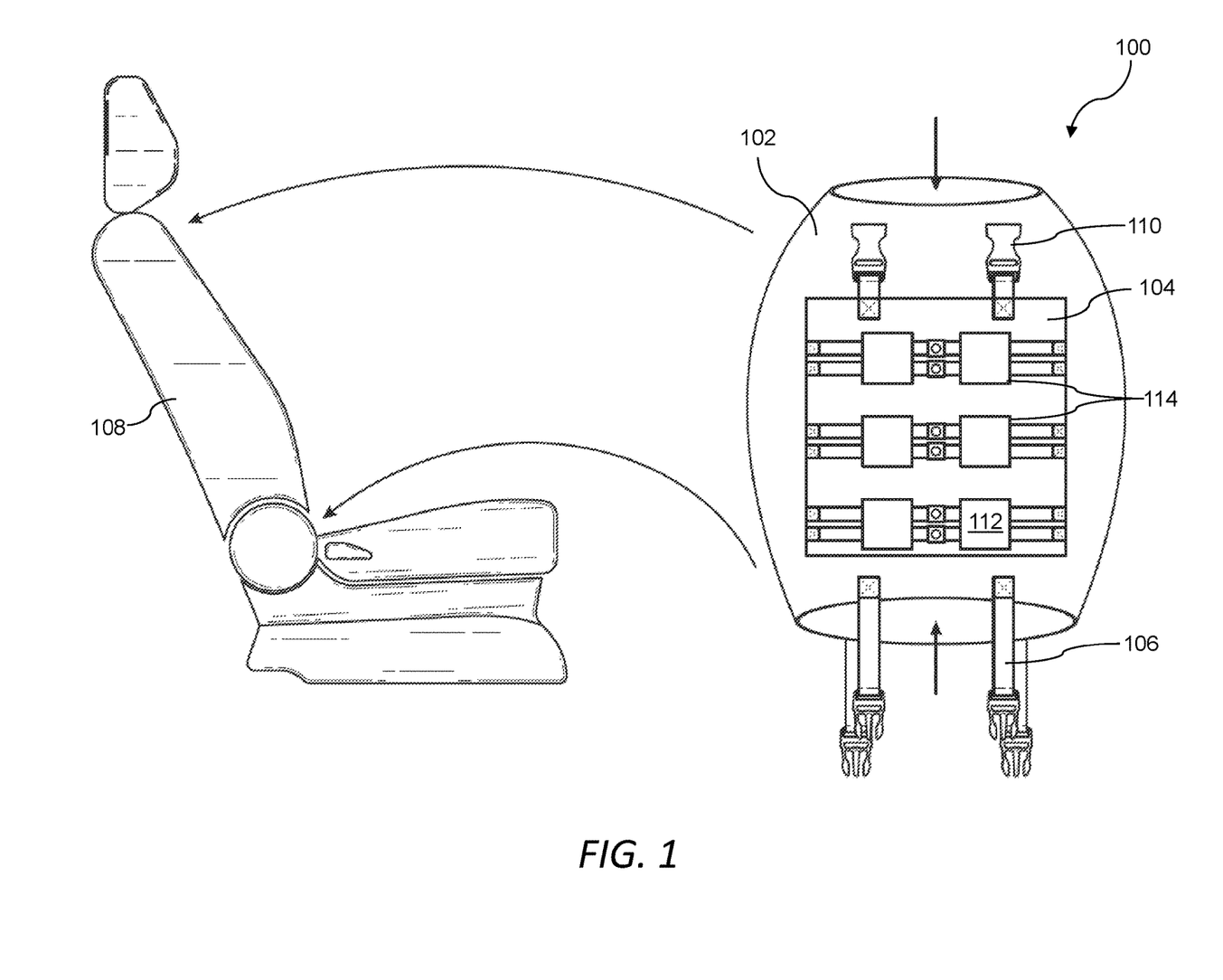
FIG. 1 shows a medical equipment adaptable travel restraint system including a carrier with a soft shell for durable medical equipment.

FIG. 1 shows a medical equipment adaptable travel restraint system 100 including a carrier with a soft shell for durable medical equipment. In general, a user may purchase a base 102 that secures to a vehicle seat 108 and a removable panel 104 for carrying equipment. In one aspect, the system 100 may be modular, such that the user may select and purchase a combination of compartments 112 that attach to the removable panel 104 in order to configure the MEATR system 100 to individual needs. For instance, some patients will require one or more internal equipment restraint systems 112 such as a first compartment shaped and sized to hold a feeding pump and one or more containment compartments 114 for feeding pump supplies. Others may require an internal equipment restraint system 112 shaped and sized to hold an oxygen saturation monitor, oxygen tank, and oxygen delivery supplies. In other embodiments, the removable panel 104 can include a pre-defined configuration of one or more internal equipment restraint systems 112, e.g., for a specific item of durable medical equipment. The internal equipment restraint systems 112 (or containment chambers 114) may have openings sufficient in size to allow the passage of tubes and wires to and from any durable medical equipment so that the equipment contained by the MEATR system 100 can be used without requiring removal from the MEATR system 100.

In general, the base 102 may be configured to secure to a seatback, either in the front of a seat 108 (e.g., in the passenger sitting area), or on the back of the seat 108. Additionally, the removable panel 104 may be configured to detach from the base 102 so that the base 102 remains semi-permanently attached to the seat, or the base 102 may be designed to travel with the removable panel 104, where both the base 102 and the removable panel 104 can be removed together for transportation of the durable medical equipment. In the latter embodiment, the base 102 may provide shoulder straps or the like for carrying on the shoulders of a user or assistant. In the former embodiment (base 102 remains on passenger seat 108), the removable panel 104 may be configured with shoulder straps for transportation, as well as hooks, buckles, and the like (e.g., to secure the removable panel 104 to a wheelchair or stroller) so CSHCN and their families can move the removable panel 104 containing the durable medical equipment freely in and out of a motor vehicle without the need to individually move each piece of equipment to an alternate carrier. In another aspect, the system 100 may include a transitional carrier such as a lightweight collapsible frame (e.g., of a fabric or mesh material) that is shaped and sized to hold the durable medical equipment, and that includes hooks or the like to couple to a wheelchair for use in transit.

The base 102 can be adapted and configured for mounting to a motor vehicle seat 108 (e.g., a bucket seat, a bench seat, and the like). The seat 108 can be a front row seat, second row seat, third row seat, and the like and can be positioned in front of or beside a user of the system 100. For example, the base 102 can be a sleeve adapted and configured to slide over an upright seat back. The base 102 can include one or more elastic regions to stretch and accommodate a variety of differently shaped automobile seats without the need for straps and potential bunching of loose materials. The base 102 may also or instead include connectors such as adjustable straps, drawstrings, cinches, or the like to secure the base 102 in a desired position on the seat 108.

In some embodiments, the base 102 includes one or more openings or frangible regions adapted and configured for placement over a side torso airbag (also known as "side-impact" or "side thorax-abdomen" airbags) to permit deployment of the side torso airbag after placement of the base 102. For example, an opening or seam can be stitched with a thread and/or pattern having sufficient strength to accommodate placement over a seatback, tensioning with straps, and/or coupling with the removable panel 104, but designed to rupture under the forces generated by side torso airbag such that the side torso airbag will expand through the opening. More generally, the base 102 and/or removable panel 104 may be configured to cooperate with active and passive vehicle restraint systems including seat belts, three-point restraints, side air bags, front air bags, rear seat air bags, and so forth.

In one embodiment, the removable panel 104 can have a three-dimensional structure and/or enclosure that can resemble a suitcase (e.g., a hard or soft suitcase, or a backpack). Such an embodiment can be placed on a front or rear motor vehicle seat and secured using a seatbelt and/or LATCH/ISOFIX system as discussed herein. For example, a shoulder and lap seatbelt can pass through one or more slits/pathways within or on the suitcase before engaging with a buckle.

In some embodiments, the base 102 includes one or more straps 106 and/or buckles to further secure the base 102 to the seat 108. For example, the straps 106 can extend from opposite sides of the base 102 under the motor vehicle seat 108. In some embodiments, the straps 106 are adapted and configured for coupling with one or more anchors on the seat 108. For example, the base 102 can include two clips or other connectors adapted and configured for engaging ISOFIX lower anchors and a top tether strap adapted and configured for engaging an ISOFIX upper anchor. ISOFIX is an international standard for attachment points for child safety seats in passenger vehicles. The system, also called "Lower Anchors and Tethers for Children" or LATCH in the United States, specifies an anchoring system defining standard attachment points including two lower anchors (e.g., steel loops) and a top anchor, which are collectively designed to secure a combined weight of an infant and car seat under predetermined crash conditions (e.g., frontal crash at thirty miles per hour) with a weight from eighteen to thirty-seven kilograms depending on the type of car seat. While these standards were designed for infant car seats rather than durable medical equipment, they provide a convenient and nearly universal mechanical framework for securing items of similar weights during a car crash.

The durable medical equipment contemplated herein may vary from one pound to twenty-five pounds individually (e.g., for a feed pump accessory or a large oxygen tank, respectively) and from five pounds to forty pounds in the aggregate (e.g., including batteries, hoses, feedbags, and other accessories for use with the durable medical equipment). Thus, the ISOFIX systems devised for infant car seats are also suitable for use with durable medical equipment described herein. And the ISOFIX anchors are well-suited for quickly, conveniently, and securely attaching a medical equipment container such as the base/panel 102/104, or any other suitable carrier such as any of those described herein to a vehicle in a manner that prevents the carrier from becoming a dangerous projectile or explosive during a crash. It will be appreciated that the ranges provided above are examples only, and the durable medical equipment and/or accessories used with the removable panel 104 may be lighter (e.g., 0.5 pounds) or heavier (e.g., 40 pounds) than these examples.

It will be understood that the secure attachment mechanisms provided by, e.g., ISOFIX anchors are useful in the context of medical device transportation. However, in order to facilitate secure, crash-safe transportation, a carrier also preferably includes an internal equipment restraint system for securely restraining an item of durable medical equipment such as a medical oxygen tank system within an interior of the carrier during a crash. The carrier may also or instead include any configuration of connectors such as anchors, straps, buckles, sleeves, or the like for securing an item of durable medical equipment on the outside of a carrier such as the removable panel 104. Thus, for example, an oxygen tank may usefully be retained within a harness on the outside of a removable panel 104, or otherwise secured to the outside of a carrier.

The base 102 and the removable panel 104 can include one or more (e.g., 2, 3, 4, 5, 6, 7, 8, and the like) connectors 110, such as complementary buckles, side-release buckles, clips, straps, or other couplers or the like, as well as combinations of these, that removably and replaceably attach the removable panel 104 to the base 102. For example, the connectors 110 can be distributed around the base 102 and the removable panel 104 in order to prevent or minimize movement of the removable panel 104 relative to the base 102.

The removable panel 104 may usefully incorporate an internal equipment restraint system 112 configured to hold durable medical equipment in a crashworthy manner, along with one or more additional containment chambers 114 shaped and sized to store accessories associated with the durable medical equipment. In this context, it will be understood that the internal equipment restraint system 112 and the containment chambers 114 are discussed separately, and are intended to refer to a restraint system for a large item of durable medical equipment and containers for other smaller, lighter, and/or more numerous medical accessories. However, the internal equipment restraint system 112 and the containment chambers 114 may, in certain instances, be similar or identical provided that they can respectively secure any corresponding medical equipment and accessories in a crash-safe manner.

In some embodiments, the internal equipment restraint system 112 and/or the containment chambers 114 may be permanently attached to (e.g., by stitching, adhesives, rivets, etc., or any combination of these) the removable panel 104 and/or defined by the removable panel 104. In other embodiments, the internal equipment restraint system 112 and/or containment chambers 114 may be removably attached to the removable panel to provide a modular or reconfigurable carrier. In this latter embodiment, the connectors may be attachment points employing the U.S. Army's MOLLE (Modular Lightweight Load-carrying Equipment) system described in U.S. Pat. No. 8,523,29 and U.S. Patent Application Publication Nos. 2015/0189977 and 2016/0143425 or other system such as those described in U.S. Patent Application Publication Nos. 2013/0126566 and 2016/0040958. Each of the preceding patents and patent applications is incorporated by reference herein in its entirety.

The containment chambers 114 may be adjustable or sized for a particular piece of medical equipment or accessory, and multiple containment chambers 114 can be selected and attached to the removable panel 104 based on a user's particular needs. One or more of the containment chambers 114 may include a non-slip internal surface (e.g., rubber, rubberized textiles, and the like) to more securely retain objects therein. Additionally or alternatively, one or more of the containment chambers 114 can include a tether, strap, drawstrings, and the like for closing an upper opening in the containment chambers 114 or otherwise securing objects within the containment chambers 114 against displacement during transportation.

The internal equipment restraint system 112 may similarly include non-slip surfaces or connectors such as tethers, straps, drawstrings, and so forth to securely retain durable medical equipment within the removable panel 104 and secured to the base 102. Such embodiments can be particularly useful for retaining medical gas (e.g., oxygen) tanks, suction receptacles, suction pumps/aspirators, and other large or heavy items of durable medical equipment.

Figure 2:
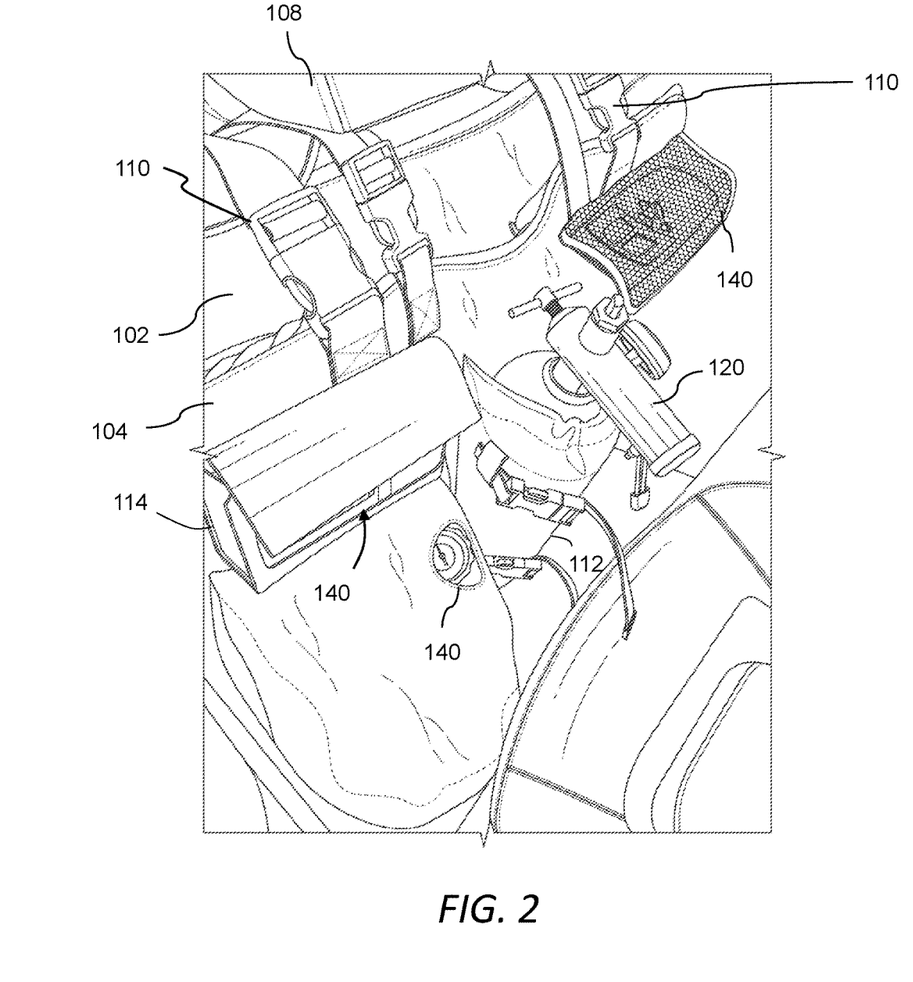
FIG. 2 shows a medical equipment adaptable travel restraint system positioned on the back of a passenger seat of a vehicle.

FIG. 2 shows a medical equipment adaptable travel restraint system positioned on the back of a vehicle seat. In general, the removable panel 104 may include an internal equipment restraint system 112 to retain durable medical equipment 120 such as a portable oxygen tank. The removable panel 104 may be coupled through one or more connectors 110 to a base 102 that fits over the back of a passenger seat 108. As generally described herein, the removable panel 104 may include one or more access ports 140 for visual or physical access to the durable medical equipment 120, as well as control panels, accessories, and the like for using the durable medical equipment without removing the durable medical equipment 120 from the internal equipment restraint system. The removable panel 104 can also include one or more flaps that can couple to each other to cover the containment chambers 114, e.g., during carrying after removal from the automobile.

The base 102 can be a sleeve adapted and configured to be fitted over a standard sized motor vehicle seat back (approximate size: 27" long, 25" wide, and 8" deep), but not covering the head rest and/or side airbags. The base 102 can be made of single or double thickness of a stretch material such as neoprene with double stitching. Double stitching can provide tear resistance and strength. Openings can be reinforced with a sturdy stretch trim or the like.

The base 102 can be secured to the seat 108 using two sets of vertical woven straps and one or more horizontal straps sewn into the base 102. Clasps (e.g., with 2 or 3 complementary male and female ends) or other connectors may allow the base 102 and the removable panel 104 to be attached together, encircling and tightly securing the assembly to the seat 108 (e.g., around and/or under the seat). A fourth strap may also be attached at the top edges of the removable panel 104 and wrap around the head rest bars of the seat 108 to provide additional support.

A durable carbon fiber fabric, lined with batting and a plastic sheet (or alternately, a firm material like compressed cardboard) can form the removable panel 104, which may be engineered to provide a desired strength, durability, and form to bear the weight of the durable medical equipment 120 and accessories contained by the removable panel 104. The back side of the removable panel 104 can include one or more features for mobility. For example, a woven strap located at each end of the removable panel 104 may provide handles allowing the removable panel 104 to be carried into and out of the vehicle. Sturdy hooks or the like may allow the removable panel 104 to attach to a wheelchair or stroller. Similarly, a collapsible basket or the like may similarly be provided for transporting the removable panel 104 and its contents on a wheelchair.

The removable panel 104 can include a series of straps or other connectors that allow configuration of the removable panel 104 to accommodate the attachment and removal of the internal equipment restraint system 112 for restraining the durable medical equipment 120 (e.g., medical monitors, feeding pumps, suction apparatuses, or oxygen tanks), as well as various sized containment chambers 114 designed to hold medical accessories. The compartments can be constructed using a durable stretchy fabric and can have a sturdy trim reinforcement at the edges. A suitable clear (e.g., transparent or translucent) material (e.g., strong and durable) can be positioned over displays to provide visual ports for easy viewing of instrumentation such as displays of heart rate, respiratory rate, oxygen saturation rate, infusion rates, and so forth.

It will be appreciated that the base 102 may also be configured to secure to the lap of a passenger seat 108, e.g., via one or more ISOFIX anchors or the like in a manner similar to an infant car seat base. This arrangement permits the removable panel 104 to be connected to, and disconnected from, the base 102 through one or more other convenient mechanical connectors without requiring the user to locate and connect to the ISOFIX anchors each time the removable panel 104 is moved. In another aspect a rigid carrier, or any of the other carriers described below may also or instead be used, and may be removably and replaceably coupled to a modular base that is in turn coupled to one or more ISOFIX anchors in a passenger vehicle. In this arrangement, the vehicle restraint system described herein may also include one or more connectors for removably and replaceably coupling the carrier to the modular base.

Figure 3:
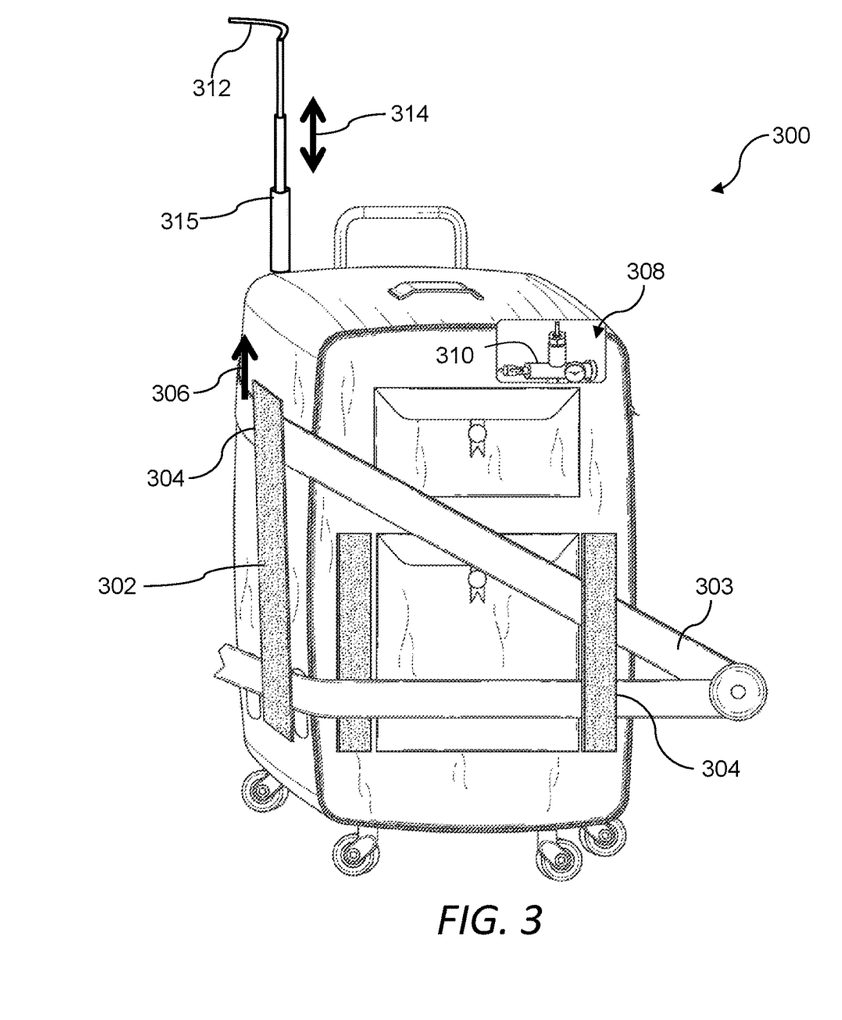
FIG. 3 shows a medical equipment adaptable travel restraint system including a carrier with a rigid shell for durable medical equipment.

FIG. 3 shows a medical equipment adaptable travel restraint system including a carrier with a rigid shell for durable medical equipment. It will be understood that the carrier 300 need not be completely rigid. Rather, the carrier 300 depicted in FIG. 3 may be relatively more rigid than the soft carriers depicted in FIGS. 1-2 (which may be formed primarily of fabrics or the like) so that the carrier 300 tends to hold its shape in the absence of external forces. In general, the carrier may include a rigid shell, a semi-rigid shell, or a non-rigid shell, e.g., formed of nylon woven material or the like. The carrier 300 may, for example, be sufficiently rigid so that the carrier 300 holds a shape in a manner similar to a suitcase or other travel item. As used herein, a "rigid" shell may include a shell capable of maintain a three-dimensional shape (e.g., 21" long, by 15" wide, by 10" deep) when empty. For example, soft luggage having plastic panels and/or wire frames is a rigid shell as contemplated herein.

Such a carrier 300 may tend to maintain its shape when vertically oriented and while containing one or more pieces of durable medical equipment. The carrier 300 may be formed in part of a rigid, durable plastic shell such as polycarbonate. This rigid material may form an exterior shell for the carrier 300, or this rigid material may form an internal skeleton for the carrier 300, surrounded for example by a fabric on the exterior and batting/padding on the interior. The fabric and padding may be reinforced with a carbon fiber or the like in order to better retain contents of the carrier 300 during a crash. The carrier may usefully be mounted on the front or lap of a passenger seat using a lap and/or shoulder seatbelt, LATCH/ISOFIX system, which may be connected to one or more connectors on an exterior of the carrier 300. In one aspect, the carrier 300 may be shaped and sized to be transported as carry-on luggage according to any relevant air travel standards, rules or regulations (e.g., nine inches by fourteen inches by twenty-two inches for U.S. carriers, including any handles and wheels, although international standards vary). In another embodiment, the carrier 300 may be shaped and sized to fit into a passenger seat of an automobile or the like.

The carrier 300, including interior and exterior finishes, may be fabricated from a variety of materials. For example, textiles for an exterior fabric, as well as straps, tethers, and the like, may be made from a variety of natural and synthetic fibers such as natural fibers, cotton, wool, silk, hemp, flax, animal hair, jute, modal, cellulose, bamboo, piña, ramie, nettles, milkweed, seaweed, metals, metal cables, manufactured fibers, monofilament, azlon, acetate, triacetate, viscose, lyocell, polycarbonate, glass, graphite carbon, carbon fiber, carbon nanotube, liquid crystal, ceramics, polyesters, aramids, para-aramids, meta-aramids, aromatic polyesters, rayon, acrylics, modacrylics, polyacrylonitrile, polylactides (PLAs), polyamides, polyamide 6, polyamide 6.6, rubber lastrile, lastol, polyethylene (PE), high-density polyethylene (HDPE), polyethylene terephthalate (PET), polypropylene (PP), polytetrafluoroethylene (PTFE), vinyl, vinyon, vinylidene chloride, polyvinylidene chloride (PVDC), polybenzimidazole (PBI), novoloid, melamine, anidex, nytril, elastoester, nylon, spandex/elastane, olefins, biosynthetic polymers, and blends of the same. Suitable aramids, para-aramids, and meta-aramids are sold under the KEVLAR® and NOMEX® brands by E. I. du Pont de Nemours and Company of Wilmington, Del., under the TECHNORA® brand by Teijin Limited of Osaka, Japan, and under the TWARON® brand by Teijin Aramid B.V. of Arnhem, The Netherlands. Suitable aromatic polyesters are available under the VECTRAN® and VECTRAN® EX brands from Kuraray America, Inc. of Fort Mill, S.C. Straps and tethers described herein can be engineered to meet anticipated loads and/or standards such as the Federal Motor Carrier Safety Administration (FMCSA) Cargo Securement Rules. In some embodiments, straps are seat-belt or climbing grade webbing.

The carrier 300 may include a vehicle restraint system 302 for coupling the carrier 300 to a passenger vehicle. For example, the vehicle restraint system 302 may include a progressive restraint system that distributes a load of the carrier—e.g., the load applied during acceleration, deceleration, or a crash by the vehicle—to multiple points along a length of a seatbelt 303 such as a three-point vehicle seatbelt when the carrier is placed in a passenger seat of a passenger vehicle and the three-point vehicle seatbelt is deployed through the progressive restraint system and around the carrier 300. For example, as shown in FIG. 3, the vehicle restraint system 302 may progressively guide the seatbelt 303 along two or more contact points 304 in order to physically distribute the load placed on the vehicle restraint system 302. This arrangement avoids a single load point that might otherwise present a point of potential failure for the vehicle restraint system 302. For example, where the seatbelt 303 is fed through webbing material or straps that are stitched on to the carrier 300, a single contact point would bear an entire lateral load (along the surface of the carrier, as indicated by an arrow 306) when the seat belt is tensioned during a collision or the like. This lateral load can be reduced by guiding the seat belt in a number of progressive steps, thereby reducing the load at any single point. In one aspect, the progressive restraint system may be configured to more generally distribute the load by retaining a three-point vehicle restraint system in contact with the carrier 300, either continuously or at a number of points on the surface of the carrier 300, e.g., with a number of different length openings to accommodate the angular, shoulder-to-waist path of a multi-point restraint.

In another aspect, the vehicle restraint system may include one or more connectors adapted to engage corresponding ISOFIX anchors in the passenger vehicle. This may include hooks, straps, or other connectors that are shaped to removably and replaceably attach to ISOFIX anchors, and that can securely retain the carrier 300 along with any durable medical equipment contained therein under standard vehicle crash testing conditions such as a frontal collision at thirty miles per hour. The vehicle restraint system 302 of the carrier 300 may also or instead include one or more straps for securing the carrier 300 to a back of a car seat as described above.

The carrier 300 may include one or more access ports 308 adapted to provide access by a user to the durable medical equipment 310 in the carrier during use. For example, an access port 308 may include an opening passing through a surface of the carrier 300 for physical access to the durable medical equipment 310. In another aspect, the access port 308 may provide physical access to a control panel for the durable medical equipment 310. Thus, for example, the access port 308 may provide an opening to operate the interface of a suction pump or feed pump, and/or to provide visual access to an information display that provides user information during operation. The access port 308 may also or instead provide a pathway for coupling electronic equipment to a battery or external power source, or may provide direct access to a plug in the electronic equipment for coupling to same. The access port 308 may also or instead provide a viewport for visual access to the durable medical equipment, which may be facilitated without providing physical access using, e.g., a clear plastic window, a mesh window of an open mesh material, or any other material or combination of materials that permits viewing of the durable medical equipment or a display or control panel for same.

The carrier 300 may also include any number of accessories 312 for medical use such as a telescoping pole 315 that extends from and retracts into the carrier 300 as shown by an arrow 314, and including an arm to hold an intravenous fluid bag or the like. The carrier 300 may also or instead include connectors such as hooks or fasteners to secure such tubing along a desired path, e.g., from a feedbag to a feed pump.

Figure 4:
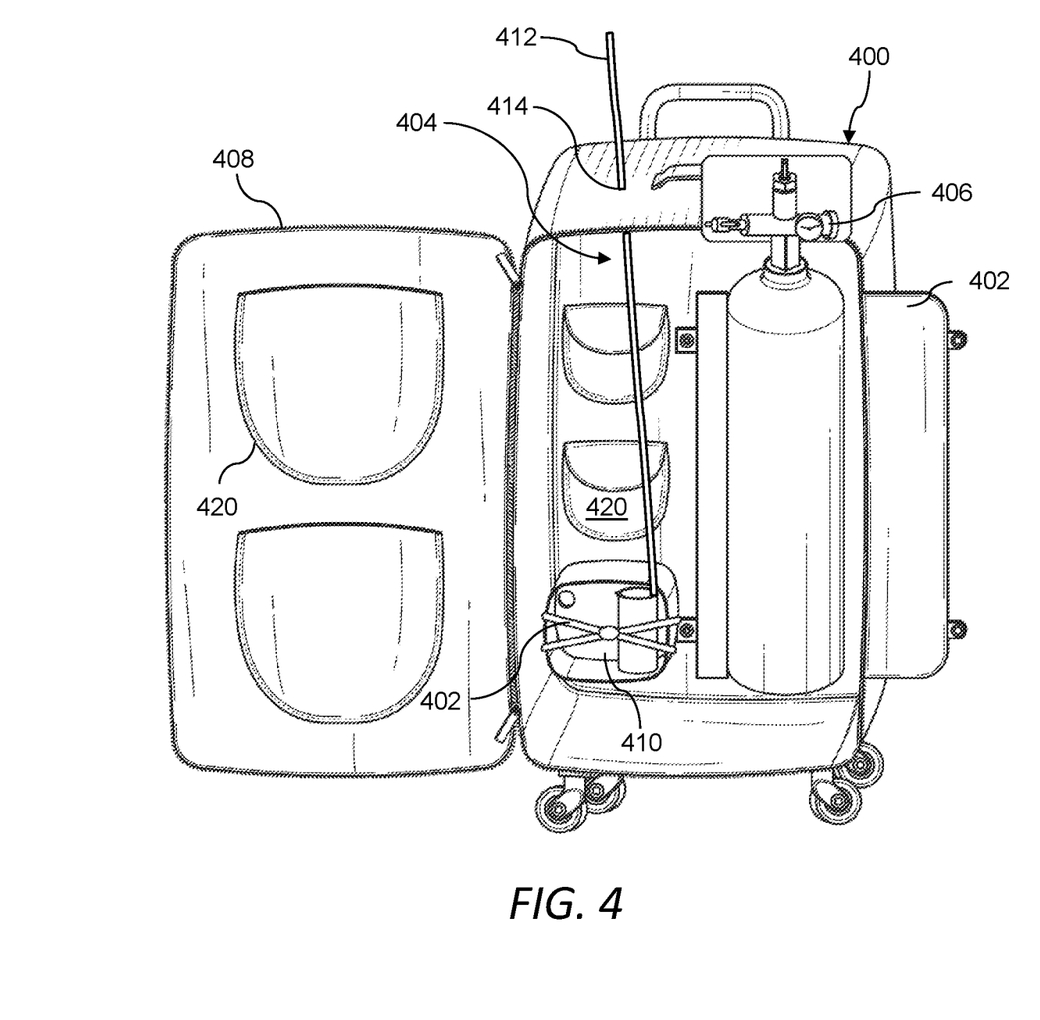
FIG. 4 shows a medical equipment adaptable travel restraint system including a carrier with a rigid shell for durable medical equipment.

FIG. 4 shows a medical equipment adaptable travel restraint system including a carrier with a rigid shell for durable medical equipment. In general, the carrier 400 may include an internal equipment restraint system 402, e.g., within an interior 404 of the carrier 400, to secure an item of durable medical equipment 406. The carrier 400 may include a recloseable section 408 such as a door, hatch, removable panel, or the like in order to selectably control exposure of, and access to, contents of the interior 404. The recloseable section 408 may be sealed with a zipper, buckles, straps, or the like for convenient transportation or storage of the carrier 400. The recloseable section 408 may also include a zipper tag or other handle or the like for opening and closing the recloseable section 408. The tag may, for example, be a large or high-visibility tag to assist access by users with various disabilities, or otherwise improve accessibility of the contents of the recloseable section 408.

The durable medical equipment 406 may include any of the medical equipment described herein. For example, the durable medical equipment 406 may include an oxygen tank, and the internal equipment restraint system 402 may be shaped and sized to secure the oxygen tank within the interior 404 of the carrier 400. The durable medical equipment 406 may also or instead include a feeding pump, and the internal equipment restraint system 402 may be shaped and sized to secure the feeding pump within the interior 404 of the carrier 400. The internal equipment restraint system 402 may also or instead be adapted for use with other durable medical equipment such as an intravenous pump, an oxygen monitor, an oxygen saturation monitor or pulse oximeter, a suction apparatus, and so forth.

The internal equipment restraint system 402 may be formed of one or more connectors such as sleeves, straps, belts, buckles, webbing, clips, harnesses, VELCRO strips, buttons, zippers, and the like, as well as combinations of the foregoing that might be used to secure the durable medical equipment 406 within the carrier 400. While a vehicle restraint system described above may secure the carrier 400 against displacement in a collision or similar event, the carrier 400 also preferably restrains durable medical equipment stored in the carrier 400 against displacement relative to the carrier 400. Thus, the internal equipment restraint system 402 may advantageously secure one or more items of durable medical equipment 406 in a crash-safe manner relative to the carrier 400 such that the carrier 400 and vehicle restraint system cooperate with the internal equipment restraint system 402 to secure durable medical equipment 406 in a crash-safe manner when the carrier 400 is placed for use and secured in a vehicle as described herein.

In general forces within the plane of vehicle travel during aggressive maneuvering may be at least 0.5 g, e.g., during hard braking or hard acceleration. During very aggressive driving maneuvers these forces may exceed 1 g or 2 g, and for a collision, these forces may be at least 5 g, at least 20 g, or more. For example, the equipment may experience a forward force of about 1-2 g during very aggressive braking, or a sideways force of about 0.5 g during aggressive turning. In a direct frontal crash at about thirty miles per hour, forces may be significantly higher, e.g., in the range of 20-30 g. And during a high-speed collision, e.g., at seventy miles per hour, the force may approach 100 g. It will be noted that the amount of force will depend on the vehicle and the event(s) creating the force. It will also be noted that the relevant design specifications will depend substantially on the type of durable medical equipment 406 being restrained. For example, a four pound feed pump during a hard braking with 2.0 g of force may apply about eight pounds of force to each of the restraint systems, either alone or in combination. However, a twenty pound oxygen tank in frontal collision that results in an immediate deceleration from thirty miles per hour to zero may apply an instantaneous force in excess of five hundred pounds to the internal equipment restraint system 402. Furthermore, the additional weight of the carrier 400 and the accessories stored therein may produce a substantially higher aggregated force on the vehicle restraint system. Thus, the carrier 400 and the various restraint systems are preferably engineered through a selection of suitable materials and assembly techniques to withstand these forces during vehicular transportation.

The durable medical equipment may generally have a weight of at least one pound, at least four pounds, at least five pounds, at least ten pounds, at least fifteen pounds, at least twenty pounds, or any weight or range of weights between these values. In one practical embodiment, the internal equipment restraint system and the vehicle restraint system cooperate to restrain the durable medical equipment against at least 1 g force in a forward direction relative to the passenger vehicle and at least 0.5 g forces in a reverse direction and a lateral direction relative to the passenger vehicle. In another aspect, the durable medical equipment 406 may include a medical feed pump system with a feed pump weighing at least five pounds, and the internal equipment restraint system 402 and a vehicle restraint system (such as the progressive restraint system described above) may cooperate to retain the medical feed pump system in the carrier 400 and the passenger seat against at least 20 g forces in a forward direction relative to the passenger vehicle and at least 0.5 g forces in a reverse direction and a lateral direction relative to the passenger vehicle. In another aspect, the durable medical equipment 406 include a medical oxygen tank system with an oxygen tank weighing at least ten pounds, and the internal equipment restraint system 402 and a vehicle restraint system (such as the progressive restraint system described above) may cooperate to retain the medical oxygen tank system in the carrier 400 and the passenger seat against at least 20 g forces in a forward direction relative to the passenger vehicle and at least 0.5 g forces in a reverse direction and a lateral direction relative to the passenger vehicle.

The internal equipment restraint system 402 may also or instead secure a suction pump 410 or the like, along with tubing 412 that leads to an access port 414 for external access.

The carrier 400 may also include one or more containment chambers 420, which may be disposed within the interior 404 of the carrier 400 as shown in FIG. 4, and/or on an exterior of the carrier 400. In general, the one or more containment chambers 420 may be formed of any of the textiles or other materials described herein, and may be adapted to store one or more accessories for the durable medical equipment 406 such as medical tubing, sanitary wipes, needles, gauze, and feed pump bags. In one aspect, at least one of the containment chambers 420 may include a window formed of a mesh material or a clear plastic (or both) in order to view contents of the containment chamber 420. At least one of the containment chambers 420 may also or instead include a reinforcement for securely retaining the contents of the containment chamber 420. For example, the reinforcement may include a flap, zipper, or the like to secure an accessory within the containment chamber 420, or the reinforcement may include a strap, webbing, or the like to secure the accessory against displacement during a collision or the like. In one aspect, one or more of the containment chambers 420 may include a zipper with a large or high-visibility tag to facilitate access by users with various disabilities, or to otherwise improve accessibility of the contents of the containment chamber 420.

Figure 5:
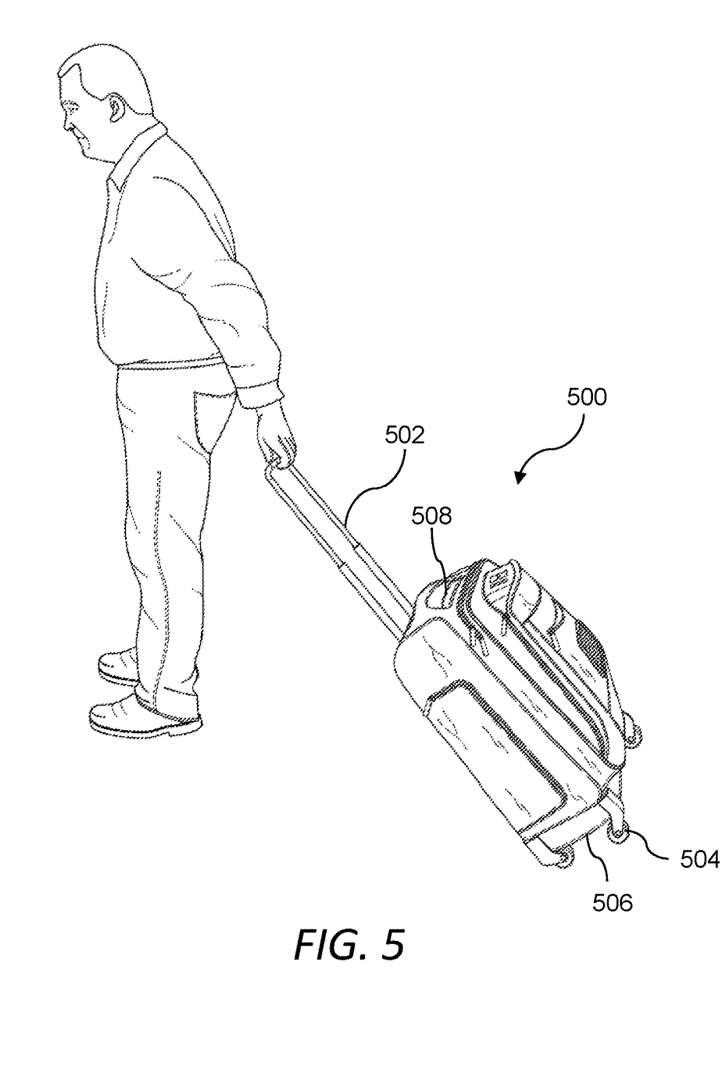
FIG. 5 shows a transportation system for a carrier of a medical equipment adaptable travel restraint system.

FIG. 5 shows a transportation system for a carrier of a medical equipment transportation system. In general, the carrier 500, which may be any of the carriers or removable panels described herein, may include a transportation system to facilitate transportation of the carrier 500 between a passenger vehicle and a deployment site where the durable medical equipment is to be used. For example, the transportation system may include a telescoping handle 502 that extends from and retracts into the carrier 500 for pulling or towing the carrier 500, along with a number of wheels 504 (e.g., on a bottom surface 506 of the carrier 500) to facilitate wheeled transportation of the carrier 500 between the passenger vehicle and the deployment site. The deployment site may be a stationary site, such as a chair, sofa, bed, or the like. Or the deployment site may be a mobile site such as a wheelchair, walker, stroller, or the like.

In another aspect, the transportation system may include one or more handles 508, loops, hooks, or the like for lifting the carrier 500 and/or for connecting the carrier 500 to a stroller, wheelchair, or other vehicle.

Figure 6:
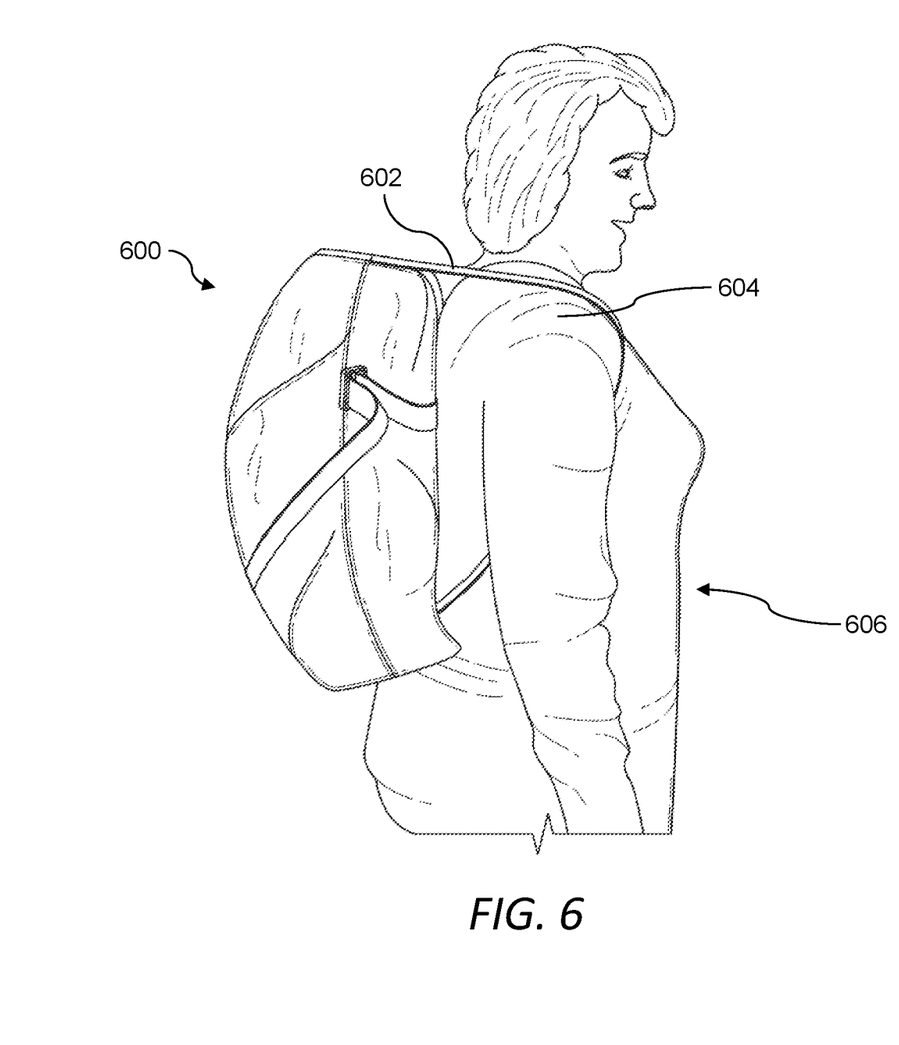
FIG. 6 shows a transportation system for a carrier of a medical equipment adaptable travel restraint system.

FIG. 6 shows a transportation system for a carrier of a medical equipment transportation system. The carrier 600, which may be any of the carriers or removable panels described herein, may include one or more shoulder straps 602 for securing the carrier 600 to shoulders 604 of a wearer 606 for transportation. The carrier 600 may also or instead include any number of waist or torso straps, pads, supports, and the like suitable for wearing the carrier 600 and transporting the carrier 600 over extended distances.

It will be appreciated that the devices, systems, and methods described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It should further be appreciated that the methods above are provided by way of example. Absent an explicit indication to the contrary, the disclosed steps may be modified, supplemented, omitted, and/or re-ordered without departing from the scope of this disclosure.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

The invention claimed is:

1. A system for medical equipment transportation comprising:
    a carrier including a rigid shell and an internal equipment restraint system formed by at least a sleeve and one or more straps for securely restraining an oxygen tank weighing at least five pounds within an interior of the carrier;
    a containment chamber on an exterior of the carrier, the containment chamber adapted to store one or more accessories for the oxygen tank, and the containment chamber including a window for viewing contents of the containment chamber;
    a progressive restraint system for distributing a load of the carrier in a vehicle crash, the progressive restraint system including multiple contact points each formed by a strap of webbing attached to the carrier and positioned to avoid a single point of contact for a seatbelt by progressively guiding the seatbelt along each one of the contact points to physically distribute a load of the carrier among the multiple contact points when the carrier is placed in a passenger seat of a passenger vehicle and the seatbelt is deployed through the straps of webbing at the multiple contact points of the progressive restraint system and around the carrier, wherein the internal equipment restraint system and the progressive restraint system are configured to cooperate to retain the oxygen tank weighing at least five pounds in the carrier and the passenger seat against at least 20 g forces in a forward direction relative to the passenger vehicle and at least 0.5 g forces in a lateral direction relative to the passenger vehicle;
    an access port in the carrier including a viewport with a mesh window providing a view of the oxygen tank and an opening adapted to provide physical access by a user to a control for the oxygen tank while the oxygen tank is in the carrier without requiring removal of the oxygen tank from the carrier; and
    a transportation system including a number of wheels and a telescoping handle to facilitate wheeled transportation of the carrier between the passenger vehicle and a deployment site.

2. The system of claim 1 further comprising shoulder straps for securing the carrier to shoulders of a wearer for transportation.

3. A system for durable medical equipment transportation comprising:
    a carrier including an internal equipment restraint system including one or more straps for securely restraining an item of durable medical equipment weighing at least five pounds within the carrier;
    one or more containment chambers adapted to store one or more accessories for the item of durable medical equipment;
    a vehicle restraint system for coupling the carrier to a passenger vehicle, the vehicle restraint system forming a progressive restraint system to distribute a load of the carrier in a crash, the vehicle restraint system including multiple contact points each formed by a strap of material attached to the carrier and positioned to avoid a single point of contact for a seatbelt by progressively guiding the seatbelt along each one of the contact points to physically distribute a load of the carrier among the multiple contact points when the carrier is placed in a passenger seat of the passenger vehicle and the seatbelt is deployed through the straps of material at the multiple contact points of the progressive restraint system and around the carrier, wherein the internal equipment restraint system and the progressive restraint system are configured to cooperate to retain the item of durable medical equipment weighing at least five pounds in the carrier and the passenger seat against at least 20 g forces in a forward direction relative to the passenger vehicle and at least 0.5 g forces in a lateral direction relative to the passenger vehicle;
    an access port in the carrier including a viewport with a window providing a view of the durable medical equipment and an opening adapted to provide physical access to a control for the durable medical equipment by a user of the durable medical equipment during use; and
    a transportation system including a number of wheels and a telescoping handle to facilitate wheeled transportation of the carrier between the passenger vehicle and a deployment site.

4. The system of claim 3 wherein the carrier includes a rigid shell.

5. The system of claim 3 wherein the carrier includes a non-rigid nylon shell.

6. The system of claim 3 wherein the vehicle restraint system includes a progressive restraint system for distributing a load of the carrier along a length of a three-point vehicle seatbelt when the carrier is placed in a passenger seat of the passenger vehicle and the three-point vehicle seatbelt is deployed through the progressive restraint system and around the carrier.

7. The system of claim 3 wherein the vehicle restraint system includes one or more connectors adapted to engage corresponding ISOFIX anchors in the passenger vehicle.

8. The system of claim 3 further comprising a base configured to be coupled to one or more ISOFIX anchors in the passenger vehicle, and wherein the vehicle restraint system includes one or more connectors for removably and replaceably coupling the carrier to the base.

9. The system of claim 3 wherein the internal equipment restraint system is shaped and sized to secure an oxygen tank.

10. The system of claim 3 wherein the internal equipment restraint system is shaped and sized to secure a feeding pump.

11. The system of claim 3 wherein the internal equipment restraint system is shaped and sized to secure one or more of an intravenous pump, an oxygen monitor, a pulse oximeter, and a suction apparatus.

12. The system of claim 3 wherein the one or more containment chambers are shaped and sized to hold one or more of medical tubing, sanitary wipes, needles, gauze, and feed pump bags.

13. The system of claim 3 wherein the access port includes a mesh window for visual access to the durable medical equipment.

14. The system of claim 3 wherein the access port includes a plastic window for visual access to a control panel for the durable medical equipment.

15. The system of claim 3 wherein the transportation system includes shoulder straps for securing the carrier on shoulders of a wearer.

16. The system of claim 3 wherein the internal equipment restraint system includes a sleeve shaped and sized to receive the item of durable medical equipment.

17. The system of claim 3 wherein the internal equipment restraint system includes a sleeve shaped and sized to receive an oxygen tank.

18. The system of claim 3 wherein the straps of material include straps of webbing.

* * * * *